(12) United States Patent
Krause et al.

(10) Patent No.: US 7,742,145 B2
(45) Date of Patent: Jun. 22, 2010

(54) METHOD AND MEDICAL EXAMINATION APPARATUS FOR EDITING A FILM CLIP PRODUCED BY MEDICAL IMAGING

(75) Inventors: Mihaela-Cristina Krause, Erlangen (DE); Uwe-Erik Martin, OT Prädikow (DE)

(73) Assignee: Siemens Aktiengesellschaft, Munich (DE)

(*) Notice: Subject to any disclaimer, the term of this patent is extended or adjusted under 35 U.S.C. 154(b) by 1028 days.

(21) Appl. No.: 11/436,272

(22) Filed: May 17, 2006

(65) Prior Publication Data

US 2006/0269275 A1    Nov. 30, 2006

(30) Foreign Application Priority Data

May 17, 2005    (DE) .................. 10 2005 022 550

(51) Int. Cl.
*G03B 21/14*    (2006.01)
*G06F 7/00*    (2006.01)

(52) U.S. Cl. .............. 352/39; 352/244; 707/1; 707/204

(58) Field of Classification Search .......... 352/38, 352/39, 244; 707/1, 7, 100, 204; 128/916, 128/922
See application file for complete search history.

(56) References Cited

U.S. PATENT DOCUMENTS

| | | | | |
|---|---|---|---|---|
| 4,685,003 A * | 8/1987 | Westland | .............. | 386/52 |
| 5,623,586 A | 4/1997 | Höhne | | |
| 6,574,742 B1 * | 6/2003 | Jamroga et al. | .............. | 713/400 |
| 6,611,846 B1 * | 8/2003 | Stoodley | .................. | 707/104.1 |
| 6,678,703 B2 * | 1/2004 | Rothschild et al. | .......... | 707/201 |
| 6,678,764 B2 * | 1/2004 | Parvulescu et al. | ............ | 710/65 |
| 2002/0026451 A1 * | 2/2002 | Lee | .......................... | 707/104.1 |
| 2002/0184238 A1 * | 12/2002 | Chylla | ..................... | 707/104.1 |
| 2003/0191766 A1 * | 10/2003 | Elin | ........................... | 707/100 |
| 2003/0194115 A1 | 10/2003 | Kaufhold et al. | | |
| 2004/0044666 A1 * | 3/2004 | Piehler | ....................... | 707/10 |
| 2004/0078236 A1 | 4/2004 | Stoodley et al. | | |
| 2004/0096110 A1 * | 5/2004 | Yogeshwar et al. | ......... | 382/239 |
| 2005/0149575 A1 * | 7/2005 | Baune | ........................ | 707/200 |
| 2007/0024752 A1 * | 2/2007 | Roush et al. | ................ | 348/565 |
| 2007/0185876 A1 * | 8/2007 | Mendis et al. | ................ | 707/10 |

(Continued)

FOREIGN PATENT DOCUMENTS

DE    41 38 188    5/1993

(Continued)

OTHER PUBLICATIONS

"Design of Multimedia Global PACS Distributed Computing Environment," Martinez et al, Proc. Of 28th Annual Hawaii Int. Conf. on System Science (1995) pp. 461-469.

(Continued)

*Primary Examiner*—William C Dowling
(74) *Attorney, Agent, or Firm*—Schiff Hardin LLP

(57) ABSTRACT

In a method and medical examination device for post-editing of at least one film clip created within an examination with the imaging medical examination device, at least one associated data item of at least one film clip is created. The data item designates the film shot and contains at least one suitable information item for the purpose of determining a specific sub-segment of the film clip.

16 Claims, 2 Drawing Sheets

U.S. PATENT DOCUMENTS

2009/0112864 A1 * 4/2009 Raichelgauz et al. .......... 707/6

FOREIGN PATENT DOCUMENTS

| DE | 43 11 791 | 10/1994 |
| DE | 101 46 576 | 9/2002 |
| WO | WO 00/33231 | 6/2000 |
| WO | WO 03/001359 | 1/2003 |
| WO | WO 2004/059536 | 7/2004 |

OTHER PUBLICATIONS

"Video Collaborative Annotation Forum: Establishing Ground-Truth Labels on Large Multimedia Datasets," Lin et al, www-nipr.nist.gov/projects/tvpubs/tvpapers03/IBM.final2.paper.pdf.

* cited by examiner

METHOD AND MEDICAL EXAMINATION APPARATUS FOR EDITING A FILM CLIP PRODUCED BY MEDICAL IMAGING

BACKGROUND OF THE INVENTION

1. Field of the Invention

The present invention concerns a method for post-editing at least one film clip created within a film record of an examination with an imaging medical examination device.

2. Description of the Prior Art

Various imaging methods are known in the medical field, with which it is possible to create sequences of moving pictures and thus films. In the process, it is often the case that, within the framework of a longer study, those scenes that are actually of interest and suitable for preparation of a diagnosis are smaller segments of the entire film with a length of for example 2-10 seconds. These individual clips must then be excised for further processing and subsequent analysis in order to then be stored separately from the original film material as diagnostically relevant scenes in a storage device.

Those segments of the entire film material that have been recognized as being diagnostically relevant are thus stored as copies of the original material in addition to the original in a medical archive. Particularly if several interesting scenes have been excised, the quantity of data to be saved is significantly increased. If a medical assistant or a physician who is working on an evaluation or report of the film exposures would like to simultaneously look at the original film and the excised scenes, he or she must download various data records from the central archive, namely the original data and the post-edited data separated as film clips. This requires additional effort and causes significantly increased data traffic in the data network, which connects the computers, terminals, etc. involved in the film processing and evaluation.

If the film segments have been excised, it is not possible to modify the scenes of interest again afterwards. The excision causes the time stamps for the beginning and the end of a scene to be uniquely defined, and they can no longer be modified. If already existing clips are now separated a second time, it is necessary to save the corresponding film data twice.

On the whole a high memory requirement arises, while at the same time the handling of the image data is made rather awkward, so that work flows become complicated in the case of a subordinate further processing and evaluation. Accompanying this are high requirements for data transfer rates in the computer networks that are used as well as in the processor performances and memory capacities of the servers or workstation computers.

SUMMARY OF THE INVENTION

An object of the present invention is to provide an improved method of the above type.

This object is achieved in accordance with the invention by a method of the type initially described wherein at least one associated separate data item of at least one film clip is created, the data item designates the film clip and at least one suitable item of information for the purpose of determining a specific sub-segment of the film clip.

As used herein, the term "data item" means any element in computer technology that can be used for the storage of one or more information items, thus in particular a file of any type, which on the basis of its data content, or on the basis of its programming technology, is suitable for fulfilling a reference function.

Such a data item is created in addition to the film clips created with the medical examination device, and this data item, on request, can be physically removed from the original film clips stored in another memory chip or in another archive. Storage of the data item together with the film clip simplifies the referencing as well as the location of a data item that has been already prepared for a film clip. One or more data items can be created, which refer to one film or several films, for example to films of a patient which can be created for one or more body parts during one or various examinations.

The separate data item refers, for example in the manner of a pointer or by its contour or its contents to one or more associated film clips, wherein the contents of this data item being designed in such a way that the contents include at least one information item, from which a specific sub-segment of the film clip or clips can be defined.

Thus it is possible, solely on the basis of the information of a data item such as a file that has been created in addition to the film clips, to mark a scene of interest relevant for later diagnostics. The excising of clips from the original data material with the problem of redundant data storage and a difficult later modification are eliminated. Thus a desired scene, for example for a subsequent report by a physician, can be extracted from the existing film material without, in addition, having to change the original material or file larger data quantities.

Information about the start and/or the duration and/or the end of a sub-segment can be stored in the data item. If the data item includes information about the start and the duration, or the duration and the end of a sub-segment, this defines a film scene and it can be easily located by means of the reference to the film clip, which is also uniquely designated. Such information items, which themselves require only little memory space, in combination with suitable software for the playback of films, can bring about the display of a film scene in the desired form.

In accordance with the invention at least one physical parameter, in particular a time stamp and/or a frame number, and/or a content related parameter, in particular a histogram distribution and/or the occurrence of a specified marker and/or specified image features and/or notes and/or the occurrence of overlays in the film clip and/or a description of the content of the sub-segment and/or a morphological reference can be stored as the information item in the data item. These different parameters among other things, can be specified as starting criteria for a scene of interest, for example, specifying a time stamp for the time elapsed since the beginning of the film clip or a frame number that specifies the number of an individual frame to be used for the definition of the scene of interest.

Also included are content-related parameters such as a specific distribution of image information or the occurrence of a marker, for example of a previously defined anatomical marker such as the hip bone or a vertebral bone, the appearance of which in the film clip allows the assumption to be made that the following images, which are also referred to as frames, are focused on the examination area of interest. The distribution of a previously administered contrast agent can be used as well as the occurrence of a specified structure in the film clips, for example a tumor, in order to define a sub-segment to be more precisely examined. A description of the content or corresponding notes on the contents of the film scene, which is more precisely defined and specified by the data item, can also be used.

It can be useful to provide software for the playback of the individual scenes or of the film clip, the software being suitable for evaluation of the information given in the data item. The software, with the help of the data stored, for example as text information, cause the frames to be played following one another. The frames, for example, can show a special morphological structure as a scene. Thus it is possible to automatically run relevant film segments for a report, which could have already been defined by the same software program that creates the data item. For this purpose image data, for example individual frames or cuts from individual frames, can be used, which then through available program can be searched for, in order to then define the start or the end of a sequence.

The information stored in the data item, can be synchronization information relating to the time sequence of a sub-segment, in particular time differences for the film start and/or film end and/or frame numbers and/or the contents of features relating to the film clip, and/or additional information supplementing the film clip, in particular text elements and/or graphic elements.

By means of the differentiation of synchronization information and additional information, both of which do not necessarily have to be specified for a film clip, the potential information of the data item to be saved can be more extensively structured, in order in this way to facilitate the overview of the stored information or to make a supplementation of the information more easily possible. The synchronization information, for example a specification about how much time has elapsed in the beginning of an interesting scene with regard to the start of the film, serves only to describe or reproduce the time sequence with regard to the scenes to be viewed as diagnostically relevant. The additional information is supplementary information in particular about the scene contents, through which, for example, an interesting region of the remaining image data in the film can be optically raised. For this purpose in the data item, if necessary using a programming language suitable for graphics or a graphic tool which in turn can be integrated into a software program, a circle, for example, can be defined, the circle surrounding a region of interest in a film segment within the film sequence. Text elements or other graphics also can be included, for example arrows or icons that are shown during the film sequence or in the viewing of a relevant scene in the relevant scene or in specified frames of the scene.

It can be of advantage to store synchronization information and additional information in different data items. This makes it easier, if necessary to comply with standardization requirements which must be fulfilled, such requirements in the medical field frequently involving clean data delimitation. This separate storage of the synchronization data as well as the additional information additionally makes various verification options available, for example after a determination of additional information by a software program suitable for editing film clips those scenes that have been marked as relevant can be shown to a physician independently from the editing by the software, in order to check whether the physician comes to a similar assessment as the software or whether another physician comes to a similar evaluation without the inserted additional information, for example with regard to the location of a tumor region or the like.

In addition, synchronization information and additional information can be stored as part of the sub-segment of the film exposure. In this case the information is treated as a part of a video clip; the corresponding data item is as such still separated from the original film exposure, but is pre-connected or otherwise connected to the entire film comparable to a digital menu of a film scene. In the process, electronic bookmarks can be used in order to refer to frames for which additional information is available.

Furthermore, frames can be replaced and/or separately stored with additional information and/or sub-regions of frames defined by additional information, corresponding frames and/or sub-regions of the original film exposure. Also in this case bookmarks can be used, by the selection of which those frames with additional information are reached. If individual frames, that is individual frames of the film clip, are used with additional information for the purpose of replacing the corresponding frames of the original film clip, this takes place in such a way that a subsequent separation of the original image information and the subsequently inserted additional information is possible at any time without great difficulties in order to acquire the possibilities of scene modification beyond synchronization.

Also, specified sub-regions of frames, for example a specified anatomical structure within an individual frame covering a larger region, can be defined by additional information, and can replace a corresponding sub-region or an entire frame of the original film clip. Here as well it is practical in the sense of a later revision of the modification to design the selection of a sub-region such that the original film material is not lost by having a corresponding frame replaced by the new frame, but instead all information of the original frame are present in the new frame, even with regard to sub-regions not shown, so that a reconstruction is again possible.

Conversely, frames and sub-regions for which additional information is available can be separately stored in order to make it obvious that editing has taken place. This storage can occur as a supplement to the storage of the original image data so that data duplication occurs only to a small degree. Alternatively, the storage can occur such that only one physically different location is used for the purpose of saving for the frame with the additional information, wherein this corresponding to a movement of this frame from the original clips, in which the additional information is still added. This also takes place in such a way that none of the information from the original data of the film clip is lost.

Thus it is possible to manipulate the scenes of interest or those scenes recognized as relevant by means of changing only the information of one or more separate data items as metadata for the film clip. The original image data as such, however, remains untouched, if the synchronization or additional information is only specified as a supplement to that information. Thus it is possible to add scenes, or to delete scenes that may overlap, or to divide them into further sub-scenes or to re-specify the beginning and the end by changing the corresponding time stamp or the like, and only a limited computing effort and therewith limited computing capacities are required.

The data item or the data items can contain information about several sub-segments of the film clip, in particular about overlapping sub-segments.

For example, it is easily possible to use a data item with which several diagnostically relevant sub-segments of the film clip are defined, for example, by storing the frame number for the beginning and the duration as information in the data item. In the process, it does not constitute a problem when the sub-segments either completely or partially overlap, because, e.g., relevant scenes to be classified in different ways blend into one another. In this context "sub-segment" means a limited segment of the film clip or the entire film clip.

The data item and/or the sub-segment can be defined by a program resource and/or a user editing and/or evaluating the film clip. Thus a user, for example a medical assistant, who is responsible for editing the film clip, can explicitly create a data item and, if necessary, name it with reference to the film segments to be described e.g., as the study of a specified body region. Alternatively the data item and desired display states within this sense can also be created by a program resource, and corresponding sub-segments, for example, can be selected by their content using imaging software which has at its disposal a pattern recognition function or an edge detection function or the like. Selection by a user is in turn possible as a supplement to or as an alternative to this.

A user can navigate between the original film clip and one or more sub-segments by means of the data item. Expediently, for this purpose a scene list can be displayed to a user in one of several data items or, for example, at the beginning of a single data item which the user can view with an appropriate program resource, if necessary with descriptive information. The list can also be graphically designed by displaying particularly relevant frames or beginning frames. Expediently, a list entry is also available that allows a viewing of the original film exposure. The navigation takes place with the help of corresponding operational tools such as, for example, a mouse pointer or a remote control.

In addition, a sub-segment can be redefined by changing at least one item of information of the data item. With this a simple modification of the selected scenes is possible, for example, by changing the information about the starting time. The sub-segment can also be redefined by changing content-related information, for example by re-specifying an anatomical structure contained in the respective sub-segment. A virtual deleting of a sub-segment is also possible by changing one or more items of information, for example by setting the duration to zero. If in spite of this the sub-segment is required again later, this change, if necessary, can be quickly undone, provided the additional information is still present in the data item. This problem can also be solved more elegantly by having an appropriate program resource make reversible deleting available.

A data item can exhibit at least one electronic bookmark which refers to a sub-segment or a frame of a sub-segment, in particular to a frame about which information is filed in a data item. Such electronic bookmarks can appear similar to a browser program for a user, so that, for example, a specified text or an icon can be clicked on, as a result of which the sub-segment or the frame is selected and, if necessary, shown enlarged or played back. Through such bookmarks of a superior data item reference can also be made to the fact that an additional data item exists for this, in which information about a respective segment or frame is stored. Thus, if necessary in the use of several data items, for example in the case of correspondingly long film clips with many relevant segments, one hierarchy of data items can be realized in a structured form.

As already mentioned a data item can include a list of sub-segments of the film clip. This list, which can be designed as text and/or graphic, can offer a user an overview of all sub-segments or of those respective sub-segments that belong together, which for example all show a correspondingly anatomical structure. The list can also be used by a program resource for playback of the corresponding scenes.

Additionally, in dependency on the information stored in the data item sub-segments and/or individual frames of the film clip can be shared for external access. Thus an external physician or specialist or also another clinic department that is also involved in the examination of a specified patient can have access via a data link or a network to relevant segments or to individual frames. For this purpose, for example, a data item can be retrieved by an external requester, causing a partial or complete sharing of the film clip. In the process frames or film segments of interest can be directly accessed, so that only the data quantity actually required for the external assessment must be transferred via the network. Also the data of the sub-segments can remain on the central archive server without it being necessary to save the data again on the computer of the external expert. Consequently memory capacities are economized, while simultaneously aspects of security law and data protection can be fulfilled.

The film clip can be created within the framework of an ultrasound examination and/or nuclear medicine examination and/or x-ray examination and/or endoscopic examination. In this connection film clips from image data of various examination methods can be combined. Typical areas in which film clips can be created are for example angiography, which is frequently performed within the scope of magnetic resonance tomography. It is also possible, e.g. in the case of endoscopic examinations, to create a virtual film afterwards from corresponding individual frame clips to be combined. For example, it is possible to make a film subsequently from clips of different layers of the subject, which are afterwards combined into an extensive data record.

In addition the invention concerns to a medical examination device which is designed for performance of the method described above. Such an examination device has devices with which film clips can be created in the medical field, such as for example an ultrasound unit or a magnetic resonance tomography apparatus. These imaging devices have connections to control systems that control the image recording and which also hand buffer data, or after performance of corresponding calculations forward the data to a central archive. Via one or more of the computing devices allocated to the photo library separate data items for the film clips are then created, which constitute references to the respective clip and which contain information about relevant sub-segments thereof. Redundant data storage is no longer necessary; in addition the corresponding sub-segments can be easily called up via the associated data items from a network.

DESCRIPTION OF THE PREFERRED EMBODIMENTS

Figure 1:
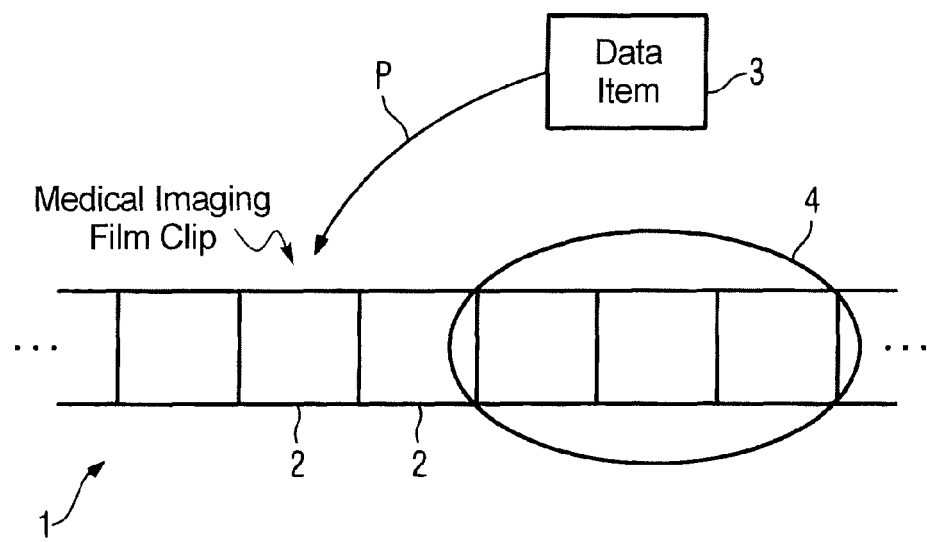
FIG. 1 shows a film clip with an associated data item for use with the inventive method.

FIG. 1 shows a film clip 1 with different frames 2 as well as an associated data item 3. The film clip 1 contains, as indicated by the dotted line on the left and on the right, additional frames 2 (not shown), so that in total a film clip 1 of a longer duration exists.

Within this longer film clip 1 a determination of diagnostically relevant sub-segments from several frames 2 is necessary for a subsequent evaluation and report.

For this purpose, a user, through a request or through an automated software program, causes a data item 3 to be created that refers to the film clip 1, as indicated here by the arrow P. This data item 3 contains information that makes the determination of a specific, diagnostically relevant sub-segment 4, symbolically represented shown here by the framing of individual frames 2. For this purpose as information in the data item 3, the number of the frame 2 beginning the corresponding sub-segment 4 is stored, in addition the number of the end frame is also stored. In addition the data item 3 contains content information about the sub-segment as a short description of the content, in particular of the anatomical structure to be taken note of or physiological operations.

Thus by storage of metadata in a data item 3, sub-segments are defined and played back without it being necessary to actually excise individual clips from the original material.

Figure 2:
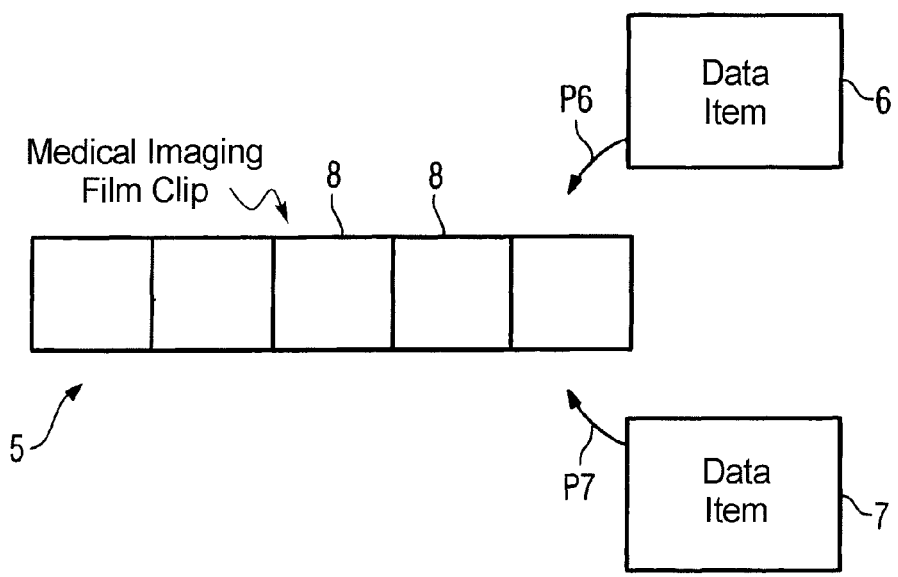
FIG. 2 shows a film clip with two allocated data items.

FIG. 2 shows a film clip 5 with two allocated data items 6 and 7, which both refer to the film clip 5, which in turn is composed of individual frames 8. This is indicated by arrows P6 and P7. Only synchronization information is stored in the data item 6, this information relating to the time sequence of several sub-segments of the film clip 5 selected by a user or a program resource.

In contrast, data item 7 contains additional information about the film clip 5, such as text elements as well as graphic elements etc., which are saved for display together with the original image data in data item 7. Thus it is possible, within a scene recognized as relevant, to make a sub-region, which, for example, shows pathological changes, recognizable by a circle or a color highlighting. The text information of the data item 7 is also displayed in addition in the sequence of the sub-segments of the film clip 5 and points out the type of a pathological change and in general the characteristic features of the selected sub-segment.

By means of the strict separation of synchronization information and additional information, a standardization in the use of such referencing data items 6, 7 in connection with film clips is facilitated.

Figure 3:
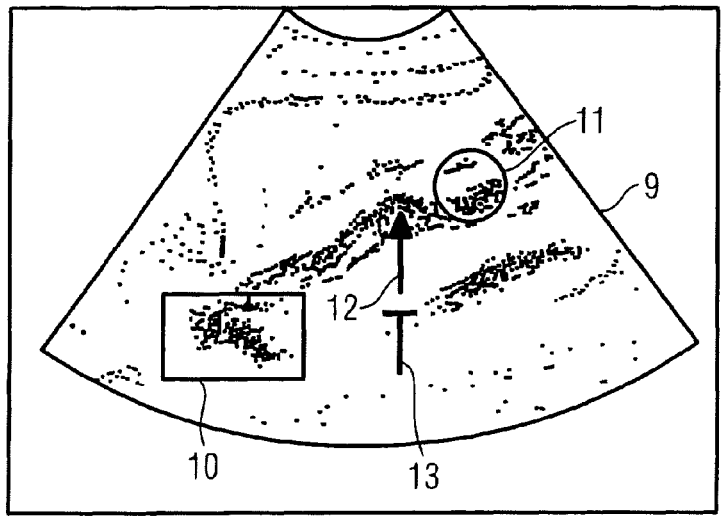
FIG. 3 shows a representation of a frame with additional information.

In FIG. 3 a representation of an individual image 9 with additional information is shown. The individual image 9 is a sub-frame of a film clip that was created with an ultrasound device. Naturally it is also possible within the scope of the invention to use sub-segments that contain only a single image.

The individual image 9 shown here is shown with additional information that a corresponding data item for additional information contains. A rectangle 10 marks a sub-region of the individual image 9, the image in which a structural change of the displayed anatomical structure is present. The circle 11 refers to a further diagnostically relevant feature of the individual image 9, which requires a more thorough examination by a physician. In addition, reference is made by an arrow 12 with an associated text statement 13 to another special feature of the individual image 9, this special feature being extensively specified by the text declaration 13. The additional information about the individual image 9, if it is a matter of graphic elements as in the case of the rectangle 10, the circle 11 as well as the arrow, is taken directly from a graphics library made available to the data item with the information. The text statement 13 is entered via the software into the data item. This takes place in a user-friendly manner as a result the text statement inserted directly into the representation of the individual image 9 by means of having the software perform the text statements itself into the data item with corresponding positioning information.

Figure 4:
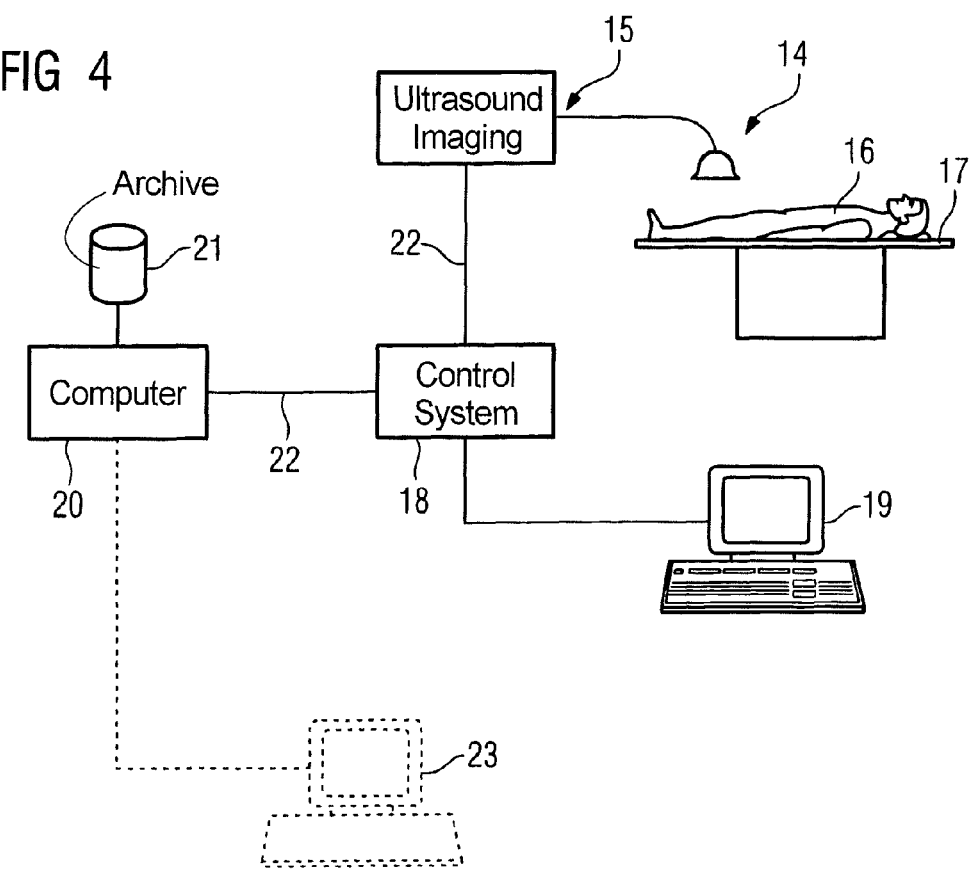
FIG. 4 shows an inventive medical examination device.

FIG. 4 shows an inventive medical examination device 14 with a device 15 for producing ultrasound images. By means of the device 15 a patient 16 lying on a patient table 17 is examined by ultrasound. The imaging function is controlled by a control system 18 that is connected to a video display 19, which permits user interaction via an interface.

The recorded data are transferred from the ultrasound imaging device 15 to the control system 18 and, using the computer 20, the data are subsequently processed for display of suitable film clips. The finished film clips are then stored in a central archive 21, which can be a system of generally accessible memory units.

Within the post-processing in accordance with the inventive method, a user (not shown) creates a separate data item using the video display 19 for the film clip stored in the central archive 21. The data item refers to this film clip. The central archive 21 is in addition accessible via other video display resources (not shown) as well as via workstation computers, so that a further post-processing can also take place by others.

The data item, which is created as well as stored with a corresponding program resource, contains information allowing the extraction of specific sub-segments from the film clip. After the post-processing, the user at the video display 19, as well as for example a physician at another workstation computer of the inventive examination device 14, has the option of accessing diagnostically relevant sub-segments as well as simultaneously accessing the original material via the data item. For this purpose only one data record in the form of the original clip is loaded, while at the same time the traffic lowing through the network indicated by the data lines 22 can be reduced.

A remotely-located person who is connected to the network via an external computing device 23 can also access the computing device 20 and therewith the archive 21 to assist in the reporting. For this purpose, first a list of the present sub-segments is accessed via the separate data item in order to download the relevant segments to be viewed for the report. Again, the network traffic is limited, which is of advantage, in particular for an external access with the limited data transfer capacities that usually apply in such a case. The original data remain unchanged and without a redundant storage thereof the central archive 21.

Although modifications and changes may be suggested by those skilled in the art, it is the intention of the inventors to embody within the patent warranted hereon all changes and modifications as reasonably and properly come within the scope of their contribution to the art.

We claim as our invention:

1. A method for editing a film clip produced by medical imaging, comprising the steps of:

for a film clip produced by medical imaging, associating a data item with said film clip that is separate from said film clip and that contains data designating said film clip; and also including in said data item an information item that determines a specified sub-segment of said film clip.

2. A method as claimed in claim 1 comprising storing information in said data item, as said information item, selected from the group consisting of information identifying a start of said sub-segment, information identifying a duration of said sub-segment, and information identifying an end of said sub-segment.

3. A method as claimed in claim 1 comprising storing in said data item, as said data designating said film clip, data selected from the group consisting of a time stamp, a frame number, a content-related parameter, a histogram distribution, an occurrence of a predetermined marker, predetermined image features, text tools notes, an occurrence of overlays in the film clip, a description of contents of said sub-segment, and a morphological reference.

4. A method as claimed in claim 1 comprising storing synchronization information in said data item selected from the group consisting of a time sequence of said sub-segment, time differences between a film start and a film end of said sub-segment, at least one frame number of said sub-segment, contents of features relating to said film clip, text elements and graphics elements.

5. A method as claimed in claim 4 comprising associating multiple data items with said film clip, and storing said information designating said film clip and said additional item of information in a first of said data items, and storing said synchronization information in a second of said data items.

6. A method as claimed in claim 4 comprising storing said synchronization information as part of said sub-segment of said film clip.

7. A method as claimed in claim 4 wherein said film clip is comprised of a plurality of frames, and wherein said information item causes replacement of one of said frames with another of said frames, as said sub-segment.

8. A method as claimed in claim 1 comprising in said data item, storing information defining overlapping sub-segments of said film clip.

9. A method as claimed in claim 1 comprising creating said data object following an input to a computerized system selected from the group consisting of a user input and an automated program input.

10. A method as claimed in claim 1 comprising using said data item in a computerized system to allow a user to navigate within said computerized system between said film clip and at least said sub-segment thereof.

11. A method as claimed in claim 1 comprising allowing a user of a computerized system to re-define said sub-segment by changing said information item in said data item.

12. A method as claimed in claim 1 comprising including in said data item an electronic bookmark that references said sub-segment.

13. A method as claimed in claim 1 comprising storing a list of a plurality of sub-segments in said film clip in said data item.

14. A method as claimed in claim 1 comprising using said data item in a computerized system to allow sharing of said sub-segment of said film clip via external access through said computerized system.

15. A method as claimed in claim 1 comprising generating said film clip using a medical imaging modality selected from the group consisting of ultrasound, nuclear medicine, x-rays, and endoscopic images.

16. A medical examination apparatus comprising:
a medical imaging modality that produces a film clip of an examination subject by medical imaging thereof; and
a control unit that automatically creates a data item for said film clip that is associated with said film clip but is separate therefrom, said data item containing data designating said film clip and an information item that determines a specified sub-segment of said film clip.

* * * * *